US008606351B2

(12) United States Patent
Wheeler

(10) Patent No.: US 8,606,351 B2
(45) Date of Patent: Dec. 10, 2013

(54) COMPRESSION OF ELECTROCARDIOGRAPH SIGNALS

(75) Inventor: Frederick Wilson Wheeler, Niskayuna, NY (US)

(73) Assignee: General Electric Company, Niskayuna, NY (US)

(*) Notice: Subject to any disclaimer, the term of this patent is extended or adjusted under 35 U.S.C. 154(b) by 0 days.

(21) Appl. No.: 13/339,277

(22) Filed: Dec. 28, 2011

(65) Prior Publication Data
US 2013/0172763 A1 Jul. 4, 2013

(51) Int. Cl.
*A61B 5/04* (2006.01)

(52) U.S. Cl.
USPC .......................................................... 600/509

(58) Field of Classification Search
USPC .......................................................... 600/509
See application file for complete search history.

(56) References Cited

U.S. PATENT DOCUMENTS

| | | | | |
|---|---|---|---|---|
| 6,081,735 | A * | 6/2000 | Diab et al. | 600/336 |
| 7,944,974 | B2 | 5/2011 | Bernard et al. | |
| 2008/0243012 | A1 | 10/2008 | Fujihashi et al. | |

FOREIGN PATENT DOCUMENTS

| | | |
|---|---|---|
| CN | 101099669 A | 1/2008 |
| CN | 101669819 A | 6/2011 |
| JP | 2007090000 A | 4/2007 |

OTHER PUBLICATIONS

Hossein Mamaghanian et al., Compressed Sensing for Real-time Energy-efficient ECG Compression on Wireless Body Sensor Nodes, The IEEE Transactions on Biomedical Engineering, vol. 58, Issue 9, pp. 2456-2466, Sep. 2011.
Sana Ktata et al., A Novel Compression Algorithm for Electrocardiogram Signals based on Wavelet Transform and Spiht, World Academy of Science, Engineering and Technology, vol. 59, pp. 855-860, 2009.
Zhitao Lu et al., Wavelet Compression of ECG Signals by the Set Partitioning in Hierarchical Trees Algorithm, IEEE Transactions on Biomedical Engineering, vol. 47, Issue 7, pp. 849-856, Jul. 2000.
Hossain, M.S. et al., ECG Compression Using Multilevel Thresholding of Wavelet Coefficients, International Conference on Intelligent Sensors, Sensor Networks and Information Processing, pp. 321-326, Dec. 15-18, 2008.
Chen, Jie et al., ECG Data Compression by Using Wavelet Transform, EICE Transactions on Information and Systems, vol. E76-D, Issue 12, pp. 1454-1461, Dec. 1993.

* cited by examiner

*Primary Examiner* — George Manuel
(74) *Attorney, Agent, or Firm* — Jenifer Haeckl

(57) ABSTRACT

A generally lossless compression system suitable for compression of data in a real-time, remote monitoring application is disclosed. In one embodiment, the real-time monitoring application is subject to a fixed-delay transmission constraint. In one implementation, a specific set partitioning method (e.g., binary tree partitioning) is employed on blocks of data that are wavelet transformed in a reversible manner so that encoded blocks may be transmitted losslessly or truncated and transmitted with some loss.

14 Claims, 5 Drawing Sheets

COMPRESSION OF ELECTROCARDIOGRAPH SIGNALS

BACKGROUND

Electrocardiograph (ECG) systems measure cardiac electrical activity associated with the muscular pumping activity of the heart. The electrical activity is measured by contacts or leads placed on the body of the patient. Typically, the measured electrical activity may then be printed out as an ECG waveform or trace for review by a doctor or diagnostician.

In hospitals, added functionality and workflow integration may be provided by digital ECG systems that acquire and store the ECG data in a digital format. The digital ECG data may be stored on various magnetic or optical devices, may be transmitted to one or more display stations remote from the patient, and may be printed once or numerous times from the stored record. The digital ECG data, therefore, provides a degree of flexibility, security, and reproducibility that may not be easily obtained from non-digital ECG system that produce only a paper record of the ECG waveform or trace.

ECG data in raw form may be too large for storage or transmission. Data compression may be applied to reduce the size of the ECG data and thus reduce the storage space requirement or transmission bandwidth requirement. When data compression is used, additional processing is required before storage or transmission to compress the data and additional processing is also required after retrieval to decompress or reconstruct the data. Data compression may be either lossless or lossy. With lossless data compression the decompressed data is identical to the original data. With lossy data compression the decompressed data may not be identical to the original data, but the goal is to make it as close as possible. When lossy compression is used the compression rate, or data size reduction, can be much larger. Whether lossless or lossy compression is appropriate depends highly on the particular application. For ECG signal compression lossless compression is generally more desirable, though lossy compression is sometimes acceptable.

Despite the benefits of digital ECG, certain vulnerabilities may be created for hospitals using the digital technology. For example, in a remote monitoring application, strict lossless reconstruction of a compressed ECG signal cannot be a guaranteed in conjunction with fixed rate transmission and real-time delivery. In particular, meeting these three criteria conflict in some circumstances. For example, it is not possible to absolutely guarantee lossless delivery of an arbitrary signal under the other two requirements (assuming, of course, that the fixed-rate available is less than what is required to send the signal samples in raw, uncoded, form). Any lossless compression system can fail under these constraints for certain ECG signals.

For example, if the ECG signal becomes very noisy over a short duration, then a lossless compressor will produce more compressed bits for that duration. If the fixed rate constraint is to be met, then the transmission delay must increase. If the transmission delay is to be met, then the fixed rate must be increased. When neither is possible, data will be lost.

BRIEF DESCRIPTION

In one embodiment, a method for compressing a data signal or signals is provided. The method comprises receiving one or more input signals and processing the input signals to generate a series of blocks. A forward wavelet transform is applied to the blocks to generate a set of wavelet coefficients. A compression algorithm is applied to the wavelet coefficients to generate a plurality of blocks of compressed data. The compressed blocks of data that are too large to be written to an output buffer are truncated. The plurality of blocks of compressed data are written to the output buffer.

In a further embodiment, an electrocardiogram (ECG) system is provided. The ECG system comprises a storage component encoding one or more processor-executable routines. The routines, when executed, cause acts to be performed comprising: receiving one or more input signals; processing the input signals to generate a series of blocks; applying a forward wavelet transform to the blocks to generate a set of wavelet coefficients; applying a compression algorithm to the wavelet coefficients to generate a plurality of blocks of compressed data; truncating compressed blocks of data that are too large to be written to an output buffer; and writing the plurality of blocks of compressed data to the output buffer. The ECG system also comprises a processing component configured to execute the one or more routines encoded on the storage component.

In an additional embodiment, one or more non-transitory computer-readable media are provided. The computer-readable media encode one or processor-executable routines. The one or more routines, when executed by a processor, cause acts to be performed comprising: receiving one or more input signals; processing the input signals to generate a series of blocks; applying a forward wavelet transform to the blocks to generate a set of wavelet coefficients; applying a compression algorithm to the wavelet coefficients to generate a plurality of blocks of compressed data; truncating compressed blocks of data that are too large to be written to an output buffer; and writing the plurality of blocks of compressed data to the output buffer.

In yet another embodiment, a method for compressing a data signal or signals is provided. The method comprises receiving one or more input signals and processing the input signals to generate a series of blocks. A forward wavelet transform is applied to the blocks to generate a set of wavelet coefficients. A binary tree partitioning compression algorithm is applied to the wavelet coefficients to generate a plurality of blocks of compressed data. The compressed data is written to a buffer without truncation.

In a further embodiment, an electrocardiogram (ECG) system is provided. The ECG system comprises a storage component encoding one or more processor-executable routines. The routines, when executed, cause acts to be performed comprising: receiving one or more input signals; processing the input signals to generate a series of blocks; applying a forward wavelet transform to the blocks to generate a set of wavelet coefficients; applying a binary tree partitioning compression algorithm to the wavelet coefficients to generate a plurality of blocks of compressed data; and writing the compressed data to a buffer without truncation. The ECG system also comprises a processing component configured to execute the one or more routines encoded on the storage component.

In an additional embodiment, one or more non-transitory computer-readable media are provided. The computer-readable media encode one or processor-executable routines. The one or more routines, when executed by a processor, cause acts to be performed comprising: receiving one or more input signals; processing the input signals to generate a series of blocks; applying a forward wavelet transform to the blocks to generate a set of wavelet coefficients; applying a binary tree partitioning compression algorithm to the wavelet coefficients to generate a plurality of blocks of compressed data; and writing the compressed data to a buffer without truncation.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

A low-complexity, wavelet-based electrocardiograph (ECG) compression system, suitable for wireless remote monitoring applications, is described herein. In one embodiment, the compression system is provided as a Binary Tree Partitioning (BTP) system that can operate over a fixed bandwidth channel, meeting a real-time signal delay specification. When it is not possible for the system to losslessly compress and transmit the ECG signals with a given fixed transmission rate and delay specification, then the system gracefully degrades to lossy reconstruction.

Figure 1:
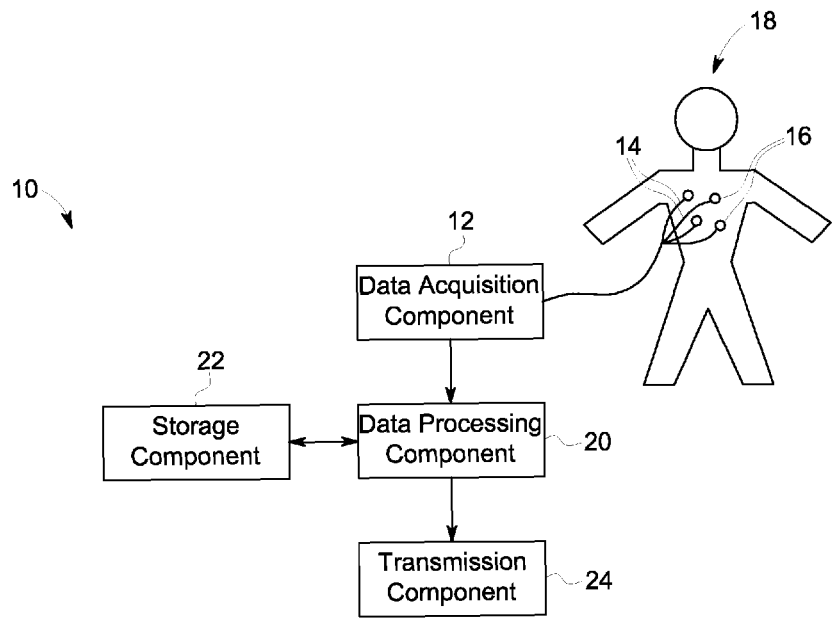
FIG. 1 depicts a monitoring system in the form of an electrocardiograph for use in monitoring cardiac electrical activity, in accordance with aspects of the present disclosure.

Turning now to the example of an ECG monitoring system, FIG. 1 depicts an ECG system 10 which may be used in conjunction with the present approach. The ECG system 10 may include a variety of components. For example, the ECG system 10 may include a data acquisition component 12 configured to receive electrical signals that convey the electrical activity of the heart, such as the polarization and depolarization events associated with cardiac contraction. The electrical signals may be conducted to the data acquisition component 12 via electrical leads 14 terminating in contact pads 16 which are positioned on the torso or elsewhere on the patient 18. While four leads 14 and contact pads 16 are depicted in FIG. 1 for simplicity, other numbers of leads 14 and contact pads 16 may be employed. In particular, twelve lead ECG systems 10 are sometimes employed in cardiac monitoring.

The ECG system 10 may also include a data processing component 20 configured to receive and/or process the electrical signals. For example, the data processing component 20 may convert analog electrical signals to digital data, may analyze the data for recurring events or for events outside of a configured threshold, and/or may process the data for visual display, such as in a waveform, chart, graph, or text presentation. In this manner, the data processing component 20 may produce secondary data, such as timing, rhythm, alert events, variance, averages, and so forth, which may be useful. Similarly, the data processing component 20 may convert the ECG data into formats suitable for storage and/or display. Further, the data processing component 20 may include one or more circuits or may execute one or more stored processor-executable routines that facilitate transmission of the ECG data to a remote monitoring site. For example, the data processing component 20 may employ binary tree partitioning, as discussed herein, as part of an ECG signal compression protocol used to facilitate remote monitoring of an ECG signal. In certain embodiments, the processed ECG data may be transmitted to a remote site using one or more transmission components 24, such as antennas or network connections employing suitable protocols, circuitry, or other communication structures or standards used in the transmission of data.

The processed ECG data may also be stored in a storage component 22, such as one or more memory chips, magnetic or solid state drives, optical disks, and so forth, for short or long-term storage. The storage component 22 may be local or remote from the data processing component 22 and/or data acquisition component 12. For example, the storage component 22 may be a memory or storage device located on a computer network that is in communication with the data processing component 20. In the present context, the storage component 22 may also store programs and routines executed by the data processing component 20, including routines for implementing the presently disclosed data compression approach.

In one implementation, the ECG system 10 may be utilized as part of a fixed bandwidth wireless real-time cardiac monitoring system. Desirable features of such a monitoring system may include one or more of the following:

(1) Low data rate (high data compression)—If the compressed data rate is lowered, each transmission component 24 requires a smaller bandwidth and uses less power.

(2) Capability to operate in real-time over a fixed-rate channel—Some wireless monitoring systems connect the ECG monitor and the base station with a fixed bandwidth channel. This is a challenge for the compression system. There is an inherent tradeoff between the fixed rate required for lossless compression and the encoder's output data buffer size, or real-time delay. Remote monitoring systems can be part of an emergency response chain. Since response time may be an issue, the compression system should add as little delay as possible between signal acquisition and display.

(3) High availability of lossless reconstruction—The ECG signal sample rate and quantization (A/D) are typically designed to achieve a signal quality level corresponding to the needs of a particular diagnostic purpose. So, any data compression scheme should strive to maintain that signal quality level. This may be particularly true in wireless monitoring applications. If the diagnostic accuracy of the ECG signals could be maintained with a reduced sample rate, or a reduced number of bits per sample, then those parameters would likely have been scaled accordingly in design.

(4) Graceful degradation—Any fixed-rate, real-time compression system has some probability of becoming lossy, even if it is lossless by general design. If it is not possible to transmit and reconstruct the ECG signals without loss, then the degradation should be graceful, without sudden gaps in the signal. Instead, the reproduction fidelity or signal quality level should be gradually reduced without abrupt changes.

(5) Low computational complexity—In certain wireless cardiac monitoring systems, the ECG may be recorded, processed and transmitted by a battery operated device. With lower complexity algorithms, battery energy is conserved.

With these criteria in mind, an embodiment of a compression system as discussed herein, such as a Binary Tree Partitioning (BTP) system, may address one or more of these issues. For example, in one implementation, an embodiment of a BTP system provides lossless compression with a high compression ratio and graceful degradation. The BTP system parameters can be selected such that ECG signals are compressed, transmitted over a fixed rate channel, received within a certain time delay, and generally reproduced losslessly. When the ECG signal cannot be delivered losslessly within the constraints (such as due to intermittent excessive ECG signal noise), then the signal is delivered with some loss, but with as much fidelity as is possible. Further, though one implementation of the present approach is in the context of fixed-rate and real-time delivery, the core BTP algorithm can also be used for ECG signal compression for storage, where these requirements do not pertain. This may be done by removing the buffering and data truncation portions of the system, as discussed herein. In such a storage mode, the recovered ECG signal would be lossless at all times.

Figure 2:
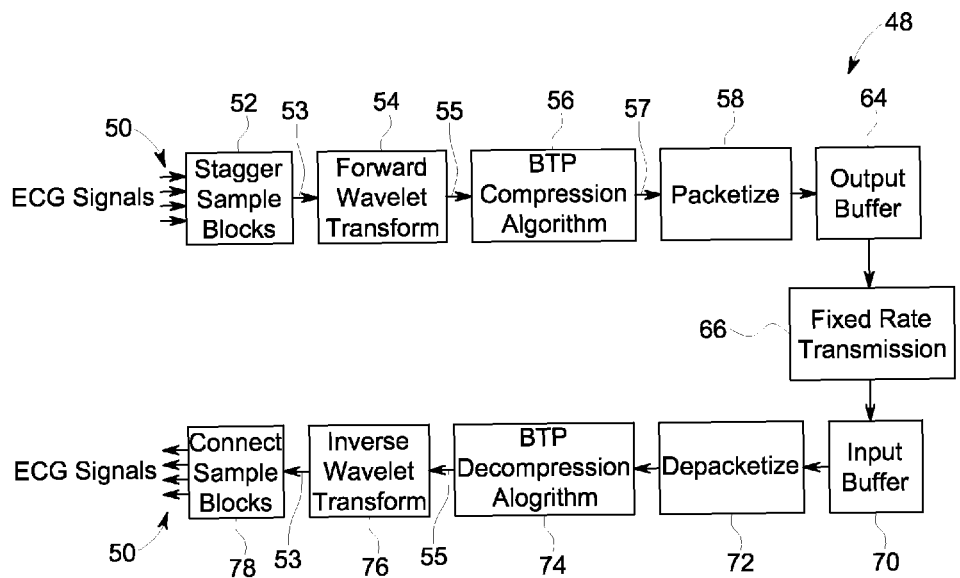
FIG. 2 depicts a block diagram of a BTP system, in accordance with aspects of the present disclosure.

As discussed herein, the data compression system (e.g., the BTP system 48) is the overall system that encompasses the handling of the ECG signals, the wavelet transform, compression with the BTP algorithm, buffering and truncation, and packetization. Conversely, as used herein, the BTP algorithm encodes wavelet coefficients to a bitstream (and reverses the procedure). With this in mind, FIG. 2, depicts an overall block diagram for an embodiment of a BTP system 48. In this example, the ECG signals 50 are split (block 52) into staggered blocks 53, then decorrelated with a wavelet transform (block 54). As will be appreciated, staggering the blocks is optional and, in other implementations, the blocks may not be staggered. The BTP algorithm (block 56) then compresses the wavelet coefficients 55. The compressed data 57 is packetized (block 58) and placed on an output buffer 64 to await transmission. After transmission (block 66), the decoder reverses each of the encoding steps to reconstruct the ECG signals 50. That is, the transmitted data is placed in an input buffer 70 and depacketized (block 72). The wavelet coefficients 55 are decompressed (block 74) and undergo an inverse wavelet transform (block 76) to reproduce the blocks, such as the staggered blocks 53 in the depicted implementation. The blocks are then reconnected (block 78) to reconstruct the ECG signals 50.

In certain embodiments discussed herein, the BTP algorithm uses an integer lifting-based implementation of the wavelet transform, allowing lossless compression. Further, in at least one embodiment the BTP system 48 has additional bitstream structure and a buffering component (relative to conventional systems) to provide real-time delivery over a fixed rate channel criteria. One result is that the fixed rate channel may be at times underutilized in such implementations.

With the foregoing discussion of FIG. 2 in mind, additional details of an embodiment are provided by way of example. With respect to the sample block generation (block 52), the digitized ECG signal 50 may be represented by a sequence of signed integer values. For monitoring applications, the sample rate is usually 120 Hz and the samples are quantized to 10 bit integers representing a range of 10 mV. An ECG record consists of $N_S$ synchronized signals from the same patient. For monitoring applications, there are usually $N_S$=4 derived signals that need to be transmitted.

In an implementation of a BTP system 48, each ECG signal 50 is divided into blocks of B consecutive samples (e.g., B=64). Each block of samples from each signal is compressed independently. In one implementation, the blocks of each signal are staggered to distribute the computational tasks required at the end of each block for each signal. This staggering of the blocks is optional, however, and in other implementations the blocks may not be explicitly staggered. Coding blocks separately will facilitate synchronization and resynchronization.

With respect to the wavelet transform employed in certain implementations, such a transform may be employed in compression for various reasons, For example, for natural signals the wavelet transform generally results in a sparse representation in which a few large coefficients dominate and most coefficients are small or near zero. In addition, there is generally reduced data correlation in the wavelet domain. These effects of the wavelet transform are one way in which a compression system can exploit the correlation of the signal. The correlated signal samples are converted to coefficients that are uncorrelated and on the average have lower magnitudes. For natural signals, high energy coefficients tend to cluster in the wavelet domain. Likewise, low energy coefficients tend to cluster. The BTP algorithm compresses the signals by exploiting this clustering of low energy coefficients.

As will be appreciated, in certain approaches predictive coding may be an alternative to transform coding, which is the type of coding described here. However, for the purpose of explanation herein, use of the wavelet transform is discussed for the BTP system 48 because, when coupled with a bitplane coder like a BTP algorithm, it allows the system 48 to gracefully degrade when some of the compressed data must be dropped. However, as will be appreciated, in an implementation where predictive coding is employed a predictive system may also be designed which gracefully degrades. As such implementations employing predictive coding are also encompassed by the present disclosure.

Figure 3:
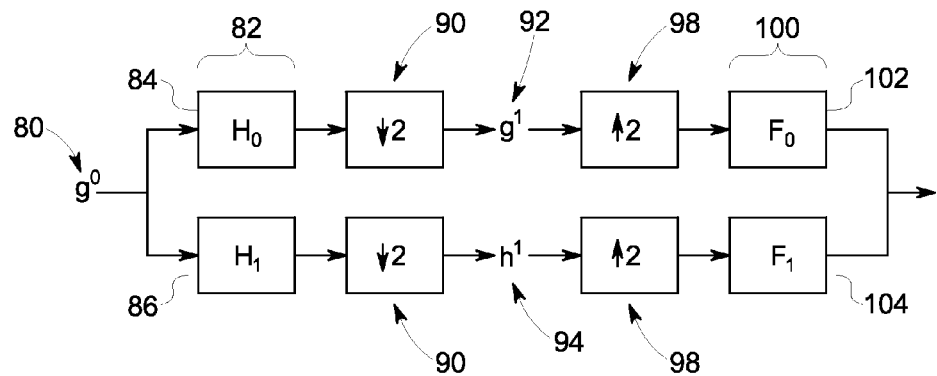
FIG. 3 depicts a filter bank implementation of a wavelet transform, in accordance with aspects of the present disclosure.

The wavelet transform (block 54) may be implemented with filter banks. Turning to FIG. 3, the structure of one such implementation for one stage of a wavelet transform is depicted to facilitate explanation. In the depicted example, the input signal $g^0$ 80 is fed to the analysis filter bank 82, consisting of the lowpass, $H_0$, and highpass, $H_1$, filters (respectively filters 84 and 86. In the depicted example, the filtered signals undergo downsampling ($\theta 2$) 90, or removal of the odd-numbered coefficients. The result is the lowpass, $g^1$, and highpass, $h^1$, wavelet coefficients 92, 94. The signals $g^1$ 92 and $h^1$ 94 have half the rate of $g^0$ 80 so the overall number of values is preserved.

The signal $g^1$ 92 is a coarse or smoothed representation of $g^0$ 80, and $h^1$ 94 can be thought of as the additional detail information needed to get from $g^1$ 92 to $g^0$ 80. For many natural signals of interest, including ECG signals, the detail signal $h^1$ 94 has less variance than $g^1$ 92 (and $g^0$ 80), and tends to have local bursts of activity where the signal $g^0$ 80 is changing rapidly. The reconstruction process, also in FIG. 3, begins with upsampling ($\uparrow 2$) 98 which inserts zeros where the odd-numbered samples were. The synthesis filter bank 100 then interpolates with its lowpass, $F_0$, and highpass, $F_1$, LTI filters 102, 104.

For compression applications, the four filters in FIG. 3 may be designed for perfect reconstruction, so that the output of the system 48 is the same as the input, assuming $g^1$ and $h^1$ are not altered. However, this can generally only be done assuming perfect arithmetic with real numbers (not integers).

Figure 4:
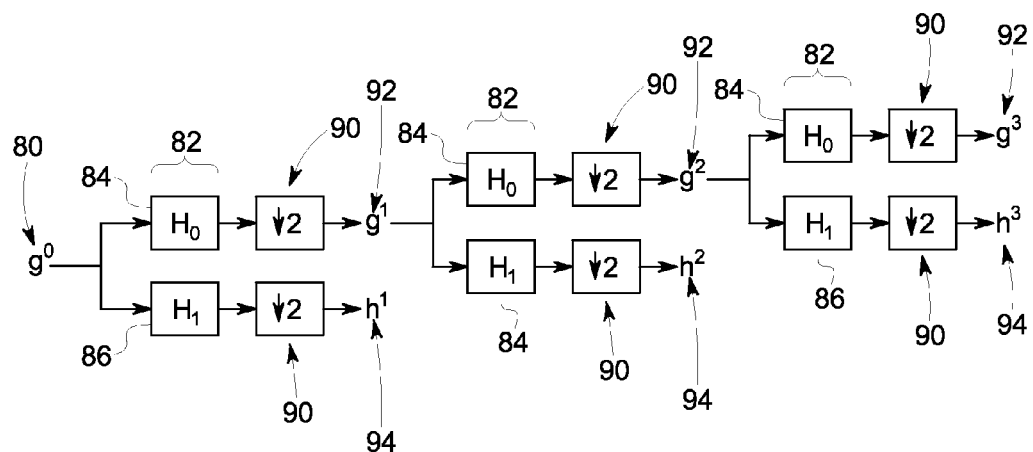
FIG. 4 depicts a 3 level dyadic wavelet transform implemented with filter banks, in accordance with aspects of the present disclosure.

Turning to FIG. 4, to make a multiresolution dyadic wavelet transform, the transform stage described with respect to FIG. 3 is applied recursively to the lowpass output, as shown in FIG. 4. For L levels, the coarse representation is further subdivided into an even more coarse or smoothed representation and an additional detail signal.

The most commonly applied discrete wavelet filters are implemented with floating point arithmetic. Once a signal is represented with floating point values, some form of quantization is required for compression. In fact, the floating point representation itself imposes some amount of quantization. This quantization step is irreversible and may prevent perfect recovery of the original sample values. Even if the original signal is integral and the wavelet coefficients are preserved to the nearest integer, the inverse transform may still not perfectly recover the original signal. This issue is not solved with a straightforward fixed point representation. However, the lifting procedure, described below, is a method to implement a perfectly reversible wavelet transform with integer values only and addresses this issue in certain implementations.

In order for the compression algorithm to be lossless, the transform should map integers to integers and be reversible. The lifting scheme is one framework for implementing a perfectly reversible wavelet transform using only integer arithmetic. In the BTP system 48, lifting is used to apply the (2,2) biorthogonal wavelet transform. This transform is nearly identical to the 5/3 integer transform, so named because the forward lowpass and highpass filters have 5 and 3 taps respectively The lifting operations take the place of filtering and filter banks. At all levels of the transform, symmetric reflection may be applied at the block edges to eliminate the sharp discontinuity while preserving perfect reconstruction.

Let $g_i^0$ for $i=0, \ldots, B-1$ denote the original block of B integer samples. In one implementation, the block size, B is assumed to be an even power of 2. The algorithm may work with more general block sizes if needed. The lifting procedure decomposes signal $g_i^l$ into the lowpass signal $g_i^{l+1}$ and the highpass signal $h_i^{l+1}$, each of which are half the length of $g_i^l$. The forward transform with lifting involves a copying operation and then two lifting steps. First, the even and odd coefficients are simply copied:

$$g_i^{l+1} = g_{2i}^l \; i=0, \ldots, B2^{-l-1}-1 \tag{1}$$

$$h_i^{l+1} = g_{2i+1}^l \; i=0, \ldots, B2^{-l-1}-1 \tag{2}$$

The first lifting step is:

$$h_i^{l+1} = h_i^{l+1} - \lfloor (g_i^{l+1} + g_{i+1}^{l+1})/2 \rfloor \; i=0, \ldots, B2^{-l-1}-1 \tag{3}$$

Thus, $h^{l+1}$ is modified based on $g^{l+1}$, which is unchanged. The second step is:

$$g_i^{l+1} = g_i^{l+1} + \lfloor (h_{i-1}^{l+1} + h_i^{l+1})/4 \rfloor \; i=0, \ldots, B2^{-l-1}-1 \tag{4}$$

where $g^{l+1}$ is modified based on $h^{l+1}$, which is unchanged. The division operations may be implemented with bit shifts. This procedure defines one stage of a wavelet transform. The multiresolution dyadic wavelet transform is implemented by recursively applying this process to the lowpass coefficients L times.

As will be appreciated, the (2,2) transform closely approximates an LTI filter bank with lowpass coefficients $-\frac{1}{8}, \frac{1}{4}, \frac{3}{4}, \frac{1}{4}, -\frac{1}{8}$ and highpass coefficients $-\frac{1}{2}, 1, -\frac{1}{2}$. The lifting implementation would exactly duplicate this filter if the floor operations ($\lfloor \cdot \rfloor$) were eliminated. However, this rounding may be employed for an integer implementation and to ensure reversibility.

The lifting framework is general and can be used to implement many linear and non-linear filters. For simplicity, only the lifting implementation of the (2,2) biorthogonal wavelet transform is described herein. In more complex implementations, lifting schemes can have more than two lifting steps and have more complicated, even non-linear, operations in each step.

The reversibility of the lifting implementation is easily demonstrated. Basically, each step can be perfectly inverted and the steps are inverted in the opposite order. The inverse transform first reverses the two lifting steps with:

$$g_i^{l+1} = g_i^{l+1} - \lfloor (h_{i-1}^{l+1} + h_i^{l+1})/4 \rfloor \; i=0, \ldots, B2^{-l-1}-1 \tag{5}$$

and:

$$h_i^{l+1} = h_i^{l+1} + \lfloor (g_i^{l+1} + g_{i+1}^{l+1})/2 \rfloor \; i=0, \ldots, B2^{-l-1}-1 \tag{6}$$

Then the values are copied:

$$g_{2i}^l = g_i^{l+1} \; i=0, \ldots, B2^{-l-1}-1 \tag{7}$$

$$g_{2i+1}^l = h_i^{l+1} \; i=0, \ldots, B2^{-l-1}-1 \tag{8}$$

In one implementation of the BTP system 48, each sample block undergoes an L level dyadic wavelet transform using the lifting implementation of the (2,2) wavelet transform. The lowpass and highpass coefficients may be concatenated into a single array, which forms an L=4 level transform:

$$g_0^4, \ldots, g_{B/16}^4, h_4^0, \ldots, h_{B/16}^4, h_0^3, \ldots, h_{B/8}^3, \\ h_0^2, \ldots, h_{B/4}^2, h_0^1, \ldots, h_{B/2}^1 \tag{9}$$

This array of B wavelet coefficients for the block is denoted by $c_i$, for $i=0, \ldots, B-1$. The coefficients $c_i$ are integers. Thus, the whole lifting procedure transforms the original block of B integer samples, $g^0$, to the array of B integer wavelet coefficients, c, and also reverses the transforms.

After the transform, conventional compression schemes may employ quantization and entropy coding. However, in one implementation of the BTP system 48 described herein, there is no explicit quantization. Instead, after the transform, the coefficients are passed directly to the BTP algorithm, which is primarily an entropy coder. However, the BTP algorithm also acts as an implicit quantizer through its graceful degradation property when its bitstream is truncated.

With regard to the BTP algorithm discussed herein, in one embodiment the core BTP algorithm converts c, the block of B integer wavelet coefficients, to a variable length bitstream. The overall approach in one implementation is to represent the wavelet coefficients in sign-magnitude form, and then to perform a compressing top-to-bottom bitplane scanning process that efficiently exploits that large clusters of wavelet coefficients will have low values. Each block of coefficients is compressed independently from each other block. The algorithm is completely reinitialized for each block.

One implementation of a BTP algorithm is described in part with concise mathematical notation that uses multiplication, division and exponentiation when convenient. However, the BTP algorithm may be implemented with few or none of these computationally costly operations. Instead, in certain embodiments, some or all of these potentially costly operations can be implemented with using bitwise shifts.

With regard to the bitplane coding, noted above, the wavelet coefficients are converted to sign-magnitude form. Let the sign of $c_i$ be represented by $c_i^S$, whose value is arbitrary and irrelevant if $c_i=0$. Let $c_i^j$, for $j=0, \ldots, P$, represent the jth bit of the magnitude portion of $c_i$. A bitplane is composed of the bits from the same bit position in all of the coefficients. So, bitplane j consists of bits $c_i^j$, for $i=0, \ldots, B-1$. The index of the most significant bitplane is P. The value P is chosen so that all possible signal blocks can be perfectly represented. The required value of P depends on the range of the samples $d_i$, the particular wavelet transform applied, and the number of transform levels, L.

One such implementation of the algorithm will work bitplane by bitplane, top to bottom, or most significant to least significant. First, information defining all of the bits in bitplane P will be placed on the bitstream, then bitplane P−1, working down to bitplane 0. When the most significant nonzero bit of a coefficient is encountered, the sign of that coefficient is placed on the bitstream.

It is this basic approach that gives the BTP approach its graceful degradation property. If the bitstream is interrupted, then a coarse reconstruction of each coefficient is possible because the most significant bitplanes are transmitted first. Sign bits are transmitted only as they are needed.

Before describing the mechanism by which each bitplane is encoded, it will help to define a concept called "significance". A coefficient is said to significant at bitplane p if its magnitude is greater than or equal to $2^p$, or equivalently, if it has a bit set in bitplane p or any higher bitplane. A coefficient is said to be newly significant at bitplane p if it has a bit set in bitplane p but not in any higher bitplane. The significance concept will also be applied to sets of coefficients. A set of coefficients is newly significant if any coefficient in the set is newly significant.

As the encoder algorithm processes each bitplane, it sends just enough information to the decoder so that the decoder will know the value of each bit in the bitplane, and the sign of all coefficients found significant so far. In the two main sections of one embodiment of the algorithm, two different types of information are sent: first significance information, then refinement bits. The significance information specifies the location of all of the newly significant coefficients for the bitplane. The refinement bits are the bits in the current bitplane for coefficients that were found significant at a previous (higher) bitplane.

At high bitplanes most coefficients are insignificant. At any bitplane, the insignificant coefficients tend to be clustered. The algorithm exploits these properties by grouping the coefficients into sets for significance testing. In one implementation, all coefficients are initially members of a single large set. This is the starting state for each new block of coefficients. Whenever a set is found to be significant, that set is split in half, and each of the new sets is tested for significance. This iterative procedure efficiently narrows in on the newly significant coefficients at each bitplane.

The encoder is provided with the coefficient values and can, thus, determine the significance of any set. The sets are tested and split in a methodical way that is duplicated at the decoder. The encoder places the result of each set significance test in the bitstream. It is these test results that determine how the sets are split and how the algorithm branches. So, reading these test results from the bitstream allows the decoder to follow along and duplicate the set splits and algorithm path taken by the encoder.

The encoder and the decoder both track the set splitting state, which is how the coefficients are currently grouped into sets. This state is kept in a length B vector. The set state $S_i$, for i=0, ..., B−1, tells how the coefficients are organized into sets. If $S_i$=n, then i is the first index of a set of $2^n$ coefficients. The values of $S_k$, for the other coefficients in that set, k=i+1, ..., i+$2^n$−1, do not matter. To initialize the set state vector, $S_0$ is set to equal $\log_2 B$ which indicates that all B coefficients are in one set. While the preceding example describes the use of a vector implementation, which is simple and avoids the use of variable sized data structures, in other implementations linked lists or stacks may be employed to store the set state information.

Figure 5:
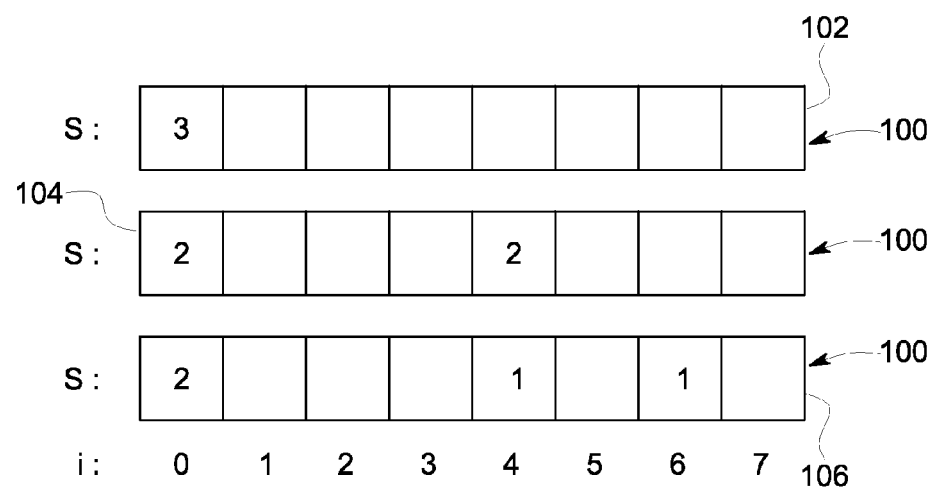
FIG. 5 depicts examples of set splitting state vectors, in accordance with aspects of the present disclosure.

FIG. 5 depicts some examples of this state vector 100. In particular, FIG. 5 depicts three examples of set splitting state vectors. In the first example 102, all 8 coefficients are in 1 set. In the second example 104, there are two sets of 4 coefficients each. Finally, in the third example 106, there is a set of 4 coefficients next to two sets of 2 coefficients. Where no value is shown for the vector, the value has no effect and may be arbitrarily initialized or set.

In one embodiment, the encoder and decoder also keep track of what is known about the significance of each set in a knowledge state vector $K_i$, i=0, ..., B−1. If $K_i$=0, the significance of the set is unknown, if $K_i$=1, the coefficient is known to be significant from a prior bitplane, and if $K_i$=2, the coefficient is newly significant in the current bitplane.

In one embodiment, the algorithm also keeps track of set significance inferences. For example, let the notation (i, n) represent a set starting at index i with length $2^n$. If (i, n) is found to be significant, it is split into two sibling sets, (i, n−1) and (i+$2^{n-1}$, n−1). These signaling sets may be referred to as being jointly significant because at least one of them must be significant since (i,n) is significant. When the first of these siblings is tested, the algorithm knows that it has a jointly significant sibling. If the first set is insignificant, the second set is automatically marked as significant, by setting $K_{i+2}^{n-1}$=1, to eliminate redundant testing For implementations discussed herein, there may be additional state variables employed by the algorithm, such as: p is the index of the current bitplane being processed, i is the index of the current set being processed, and $i_s$, if set, is the index of a jointly significant sibling.

The encoder frequently determines the significance of sets and must check some sets repeatedly. Scanning each coefficient in a set to test for significance would be computationally wasteful. Therefore, in certain implementations, the significance level of all possible coefficient sets may be precomputed.

In one such implementation, the set significance precomputation is done as follows. Sets are made up of $2^n$ coefficients for some integer n. The array of coefficients, c has B values. To help define a recursive equation $c^0$ is used as a synonym for the array c. A new array, $c^1$, with B/2 values is created according to:

$$c_i^1 = c_{2i}^0 | c_{2i+1}^0 \; i=0, \ldots, B/2-1 \tag{10}$$

where | is the bitwise OR operator. In other implementations, finding the maximum between $C_{2i}$ and $C_{2i+1}$ may be done instead of employing the bitwise operator. The above procedure of equation 10 is carried out recursively $\log_2 B$ times, using:

$$c_i^n = c_{2i}^{n-1} | c_{2i+1}^{n-1} \; i=0, \ldots, B2^{-n}-1; n=1, \ldots, \log_2 B. \tag{11}$$

In certain implementations, the encoder may need to know whether a set that starts at index i and has $2^n$ coefficients is newly significant at bitplane p. Call this binary significant test result $S_p(i, n)$. This determination can be made by testing the pth bit of $c_{i2^n}^n$. If that bit is set, then at least one of the coefficients in the set has that bit set, so the set is newly significant. All of the $c^n$ arrays are stored in one contiguous memory space, which has B−1 values. In one implementation, a short array of $\log_2 B$ pointers is used to help index that array.

To facilitate explanation, an example of pseudo-code for implementing a BTP algorithm encoder and decoder is provided below. In this example, some IF statements are provided to perform different operations depending on whether the algorithm is encoding or decoding. In this example, the difference between encoding and decoding amounts to low-level switches between reading bits and writing bits. Higher level logic for initialization, set splitting, significance inference, handling the signs, and so forth, is described, making it straightforward to combine the encoder and decoder versions of the algorithm. Actual encoder and decoder implementations of the algorithm may share code in this way.

A few aspects of the algorithm are not explicitly shown in the pseudo-code. For example, when decoding, the coefficient array is initialized to zero. No special stop conditions are explicitly shown though it should be appreciated that in an actual implementation, the decoder needs to stop if the input bitstream ends due to truncation. For simplicity, the logic for storing the input and output bitstreams (the send and receive operations below) is not shown. The example pseudo-code is as follows:

| | |
|---|---|
| Initialization | |
| set i = 0 | set index starts at the beginning |
| unset $i_s$ | initially there is no sibling set |
| set p = P | start at the highest bitplane |
| set $S_0 = \log_2 B$ | initially all coeffs. are in one set |
| set $K_i = 0, i = 0, \ldots, B - 1$ | initially no knowledge of significance |
| Main loop | |
| while p ≥ 0 | not finished with all bitplanes |
|   if $S_i > 0$ | set has more than 1 coefficient |
|     Determine the significance of the set | |
|     if $K_i = 0$ | significance of set is unknown |
|       if encoding | |
|         set b = $S_p(i, S_i)$ | find the set's significance bit |
|         send b | send the set's significance bit |
|       else | |
|         receive b | receive the set's significance |
|     else | set is known to be significant |
|       set b = $K_i$ | use the known set significance |
|     Possibly infer significance of the sibling set | |
|     if b = 0 and $i_s$ is set | this insignif. set has a jointly signif. sibling. |
|       set $K_{i_s} = 2$ | the sibling set is inferred to be signif. |
|       unset $i_s$ | |
|     Split set if it is significant | |
|     if b = 1 | this set is significant |
|       set $i_s = i + 2_i^{S-1}$ | there is a jointly signif. sibling |
|       set $S_i = S_i - 1$ | create first half size new set |
|       set $S_{i_s} = S_i - 1$ | create second half size new set |
|       set $K_i = 0$ | significance of this new set is unknown index i is not advanced here, the new set is tested next |
|     else | this set is not significant |
|       set i = i + $S_i$ | advance to the next set |
|   else | there is 1 coefficient in this set |
|     Determine the significance of the coefficient | |
|     if $K_i = 0$ | significance of set is unknown |
|       if encoding | |
|         send $c_i^p$ | send significance of this coeff. |
|       else | |
|         receive $c_i^p = b$ | receive significance of this coeff. |
|       if $c_i^p = 1$ | coefficient is newly significant |
|         set $K_i = 2$ | |
|     Handle sign of newly significant coefficient | |
|     if $K_i = 2$ | coeff. is newly signif. (possibly by inference) |
|       if encoding | |
|         send $c_i^S$ | send the sign bit |
|       else | |
|         receive $c_i^S$ | receive the sign bit |
|       set $c_i^p = 1$ | needed in case significance was inferred |
|       set $K_i = 1$ | convert from newly signif. to signif. |
|     Refine already significant coefficient | |
|     else if $K_i = 1$ | |
|       if encoding | coefficient is significant |
|         send $c_i^p$ | send the refinement bit |
|       else | |
|         receive $c_i^p$ | receive the refinement bit |
|   Possibly infer significance of the sibling set | |
|   if $K_i = 0$ and $i_s$ is set | this insignif. set has a jointly signif. sibling. |
|     set $K_{i_s} = 2$ | infer that sibling is newly significant |
|     unset $i_s$ | |
|   set i = i + 1 | advance to the next set |
| Advance to next bitplane | |
| if i > B | processed all sets in this bitplane |
| set p = p − 1 | advance to next bitplane |
| set i = 0 | start at first set in next bitplane |

Figure 6:
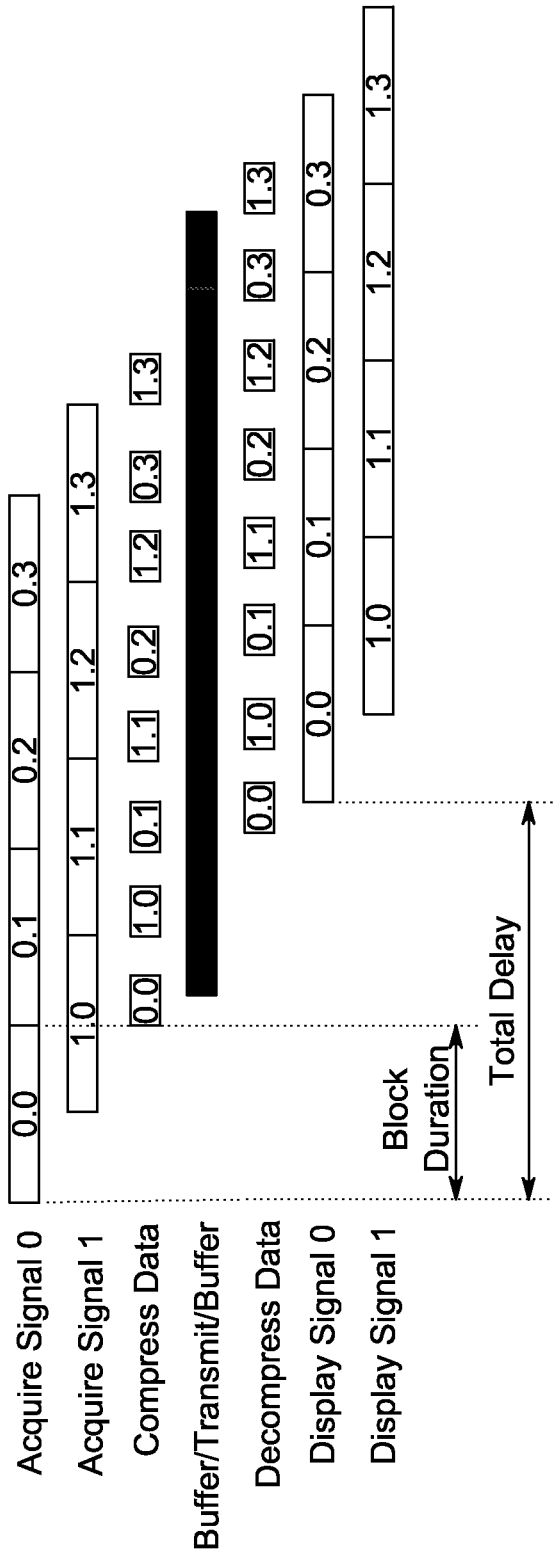
FIG. 6 depicts a timing diagram for a BTP system with 2 signals, in accordance with aspects of the present disclosure.

With regard to data buffering and transmission of a compressed signal, the amount of compressed data produced for a block of samples is variable, but the compressed data transmission rate is fixed, in accordance with certain embodiments. Therefore, a compressed data buffer may be employed to absorb some of the variability. An overall system timing diagram (FIG. 6) will help explain the buffer size calculation, discussed below. The depicted timing diagram of FIG. 6 is for a BTP system 48 with 2 signals (i.e., signal 1 and signal 2), where each time slot is labeled s, n, where s is the relevant signal number and n is the relevant sample block index In particular, in accordance with one or more implementations, the BTP system 48 uses a single buffer with size dictated by the specified real-time delay. In one embodiment, the buffer may be configured as a circular queue shared by each signal with no priority scheme. In one such embodiment, the sample blocks for each signal are staggered, so blocks become ready for compression and buffering one at a time, evenly spaced in time. Each block may place as much data as it requires on the shared buffer, so long as it will not cause overflow.

The buffer size can be determined from various system parameters, such as: the real-time delay, D (sec.); the number of signals, $N_S$; the sampling frequency, $f_s$ (Hz); the compressed data rate, R (bits per sample); and the time to compress and decompress a block, C (sec.). The total compressed data transmission rate is $RN_S f_s$ bits per second. Each data block is B samples long. By the time the last sample is input and the block can be compressed, $B/f_s$ seconds have passed, and there are $D - B/f_s$ seconds remaining before the compressed data must arrive at the decoder. In one implementation, this remaining time, less the time for computations, multiplied by the overall compressed rate gives the size of the buffer in bits:

$$S = RN_s f_s (D - B/f_s - C) \quad (12)$$

The real-time delay is at least as long as the time duration of a sample block. The sample block length is kept small so that there is time in the delay budget to acquire the sample block and then to transmit the compressed data for that block. If a sample block produces more compressed data than will fit in the buffer, then there would be a buffer overflow. When this happens, the compressed data that will not fit is truncated. As noted above, with the BTP algorithm used for compression this results in graceful degradation of the signal in that sample block. The BTP algorithm can detect a truncation with no additional side-information.

The buffer is continuously having bits removed for transmission at a rate of $RN_s f_s$ bits per second. In one implementation, when this process empties the buffer there is a buffer underflow and zeros are placed on the buffer and transmitted. This zero padding results in channel underutilization in a sense.

As noted with respect to FIG. 2, the compressed data for each sample block is packetized before being placed on the buffer. In one implementation, the BTP system 48 employs a byte-aligned scheme. A packet consists of a single byte holding the value N, the length of the packet (including the header) in bytes, followed by N−1 bytes of compressed data payload. This packetization scheme is suitable for data organization, but may not be suitable for transmission. In certain embodiments, framing for transmission occurs at a higher layer in the overall system.

Computational complexity may be a concern considering that one application is a remote wireless monitoring system where the transmitter may be powered by a battery. The computational complexity of the forward wavelet transform and BTP encoding algorithm are shown in Table 1, where operations per second assumes a sample rate of 120 Hz. The numbers given are for a single signal and should be multiplied by the total number of signals in the system (e.g., 4).

TABLE 1

| Operation | BTP | Wavelet Transform | Total | Total per Sample | Total per Second |
|---|---|---|---|---|---|
| Add | 7204163 | 839728 | 8043891 | 37 | 4469 |
| Shift | 837578 | 419864 | 1257442 | 6 | 699 |
| Increment | 1815736 | 2536114 | 4351850 | 20 | 2418 |
| Reference | 8301957 | 3006768 | 11308725 | 52 | 6283 |
| Move | 5554784 | 873588 | 6428372 | 30 | 3571 |
| Test | 8178255 | 1049660 | 9227915 | 43 | 5127 |
| Multiply | 0 | 0 | 0 | 0 | 0 |
| Total | 31892474 | 8725722 | 40618196 | 188 | 22566 |

The complexity of the encoder may be of particular interest because that is typically where a computational constraint is observed. The complexity of the reverse transform is the same as for the forward transform. The complexity of the BTP algorithm in decoding mode is comparable to the complexity in encoding mode, but, in one implementation, may be slightly less if the significance tests are only precomputed when encoding. The complexity of the BTP algorithm may be data dependent. Conversely, the complexity of the wavelet transform is independent of the specific data. This count does not include operations to move and buffer incoming samples, which occurs before the wavelet transform. Operations to move and buffer the bitstream generated are also omitted. Conversion of the samples to sign-magnitude format is omitted, as are other generally insignificant initialization operations.

The complexity operation counts used in Table 1 have been made at the C language level. Essentially, operations that are seen as tokens in a C program were tabulated. The tabulation was accomplished by adding several types of counter macros to the actual program. Logical operations (C operations &&, ||, ==and >=) were counted as adds. A reference is any array value lookup ([ ]). Any assignment (=) is counted as a move. A test operation is anything that checks for truth and possibly jumps (IF and WHILE).

Table 2 lists the major blocks of memory utilized in an implementation of a BTP encoding system given in terms of bytes. The specific size listed is for $N_s$=4 signals, a block size of B=64, a delay of D=1 sec., sample frequency F=120 Hz, rate R=6 bits per sample, and C=0 time required for computation. The decoding system does not need the B×2 bytes for the precomputed set significance vector.

TABLE 2

| Item | General size | Specific Size |
|---|---|---|
| Input Sample Buffer | $\frac{N_s^2 + N_s}{2N_s} B \times 2$ | 320 |
| Sample block being compressed | B × 2 | 128 |
| Transform workspace | B × 2 | 128 |
| Precomputed set significance | B × 2 | 128 |

TABLE 2-continued

| Item | General size | Specific Size |
|---|---|---|
| Set splitting state vector | B × 1 | 64 |
| Significance knowledge vector | B × 1 | 64 |
| Output bit buffer | $N_s$(DF − B)R/8 | 168 |
| Total | $2N_s B + 8B + N_s(DF − B)R/8$ | 1000 |

For each block of memory, the size is given as a general formula in terms of various parameters, and for a specific typical set of parameters, as given in the table caption. In one implementation, the BTP decoding system has the same memory requirements except for a slight reduction because the precomputed set significance vector is not needed.

The memory required for program instructions is not included in the table. Also omitted are a few insignificant short arrays and various scalar values used by one implementation of a BTP system 48. The formulas in the table assume that the ECG samples and the wavelet transform coefficients can be stored in 2 bytes per value.

In the depicted implementation, the set splitting state vector and the significance knowledge vector are each budgeted for 1 byte per sample in a block. However, in one embodiment, the set splitting state vector holds only small integers defining set sizes and may only need 3 or 4 bits per sample. The significance knowledge vector only holds three values, 0, 1 or 2, and thus may need 2 bits per sample. In one implementation, these two vectors could be combined to save B bytes at the expense of additional computation for bit manipulation operations.

With the foregoing comments regarding various implementations of a compression algorithm and system, various compression tests were conducted. Each of the records used for testing were approximately 30 minutes long and contained 2 signals each. Test data was obtained from the PhysioBank archive (HTTP://www.physionet.org). For testing the BTP system 48, the signals were processed to mimic signals that would be seen in actual application. One possible application for BTP is ECG monitoring, where the industry standard sample rate is 120 Hz, and quantization is 10 bits over 10 mV. Test signals were converted to this sample rate and quantization. An implementation of a transmitter may apply one or more of analog and then digital filters to the ECG signals before transmitting them. The test data was also processed to mimic the effect of these filters. The digital filters were duplicated, while analog filters were simulated with corresponding digital filters.

The MIT-BIH Arrhythmia Database records employed were originally captured with a Del Mar Avionic model 660. At capture, a 0.1 to 100 Hz analog filter was applied. That filter has a sufficiently wide passband, that its effects are negligible with respect to the present approach. The signals were sampled at 360 Hz and quantized to 11 bits over 10 mV. The first processing step was to treat the samples as real values, and to upsample the signal to 720 Hz with polyphase interpolation. This facilitates later conversion to a 240 Hz signal. Subsequent processing steps each mimicked a system processing stage of an Apex Pro telemetry system. The steps included: applying a 2.3 Hz (−3 dB) 1st order Butterworth highpass filter to the test data to simulate the 2.3 Hz (−3 dB) single pole highpass analog filter; applying a 47 Hz (−3 dB) 4th order Butterworth lowpass filter to simulate the 47 Hz (−3 dB) four pole lowpass analog filter; to get a sampling rate of 240 Hz, the test data is decimated by 3 without filtering and quantized to 12 bits over 10 mV; a 60 Hz notch filter is applied; and sample pairs were averaged to get a 120 Hz sampling rate, and the samples are quantized to 10 bits over 10 mV.

Figure 7:
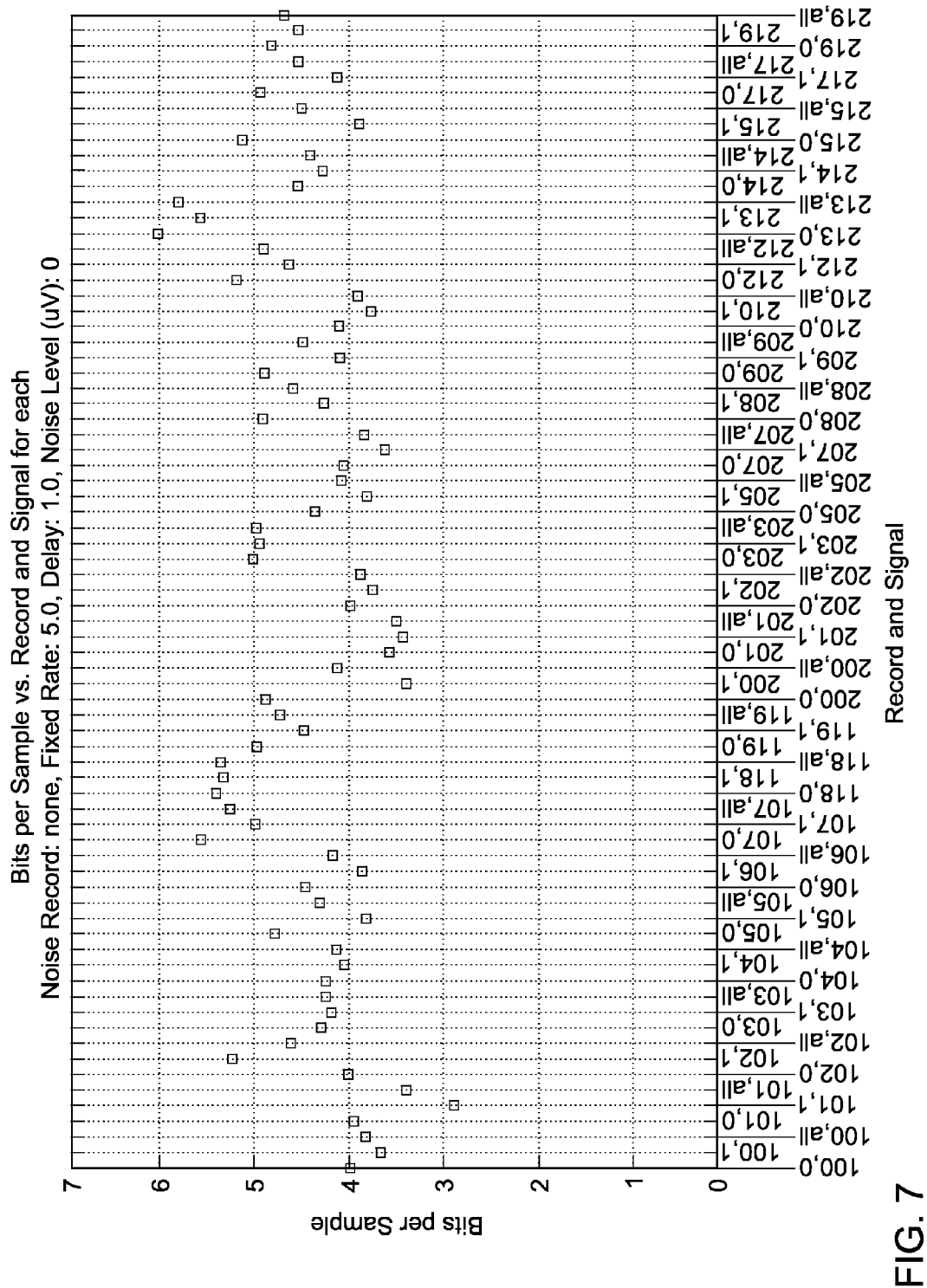
FIG. 7 depicts the overall lossless performance of a BTP coding algorithm without buffering, in accordance with aspects of the present disclosure.

Based on the experimental findings, FIG. 7 shows the overall lossless compression rate for the BTP coding algorithm for the tested records. This is the rate of all of the compressed data produced, in bits per sample, not including overhead required in a fixed rate system. Thus, this is the rate that BTP achieves if used for off-line storage.

As will be appreciated, the fixed rate needed for a lossless real-time system is larger than the overall lossless compression rate. A real-time system does not average the rate over the entire signal, and instead must have a high enough rate to transmit short noisy segments, that do not compress well, within the time constraint.

The effect of varying the real-time delay on the performance of the BTP system 48 was also tested. For certain records, the change in delay was not found to substantially affect the performance. For other records there was not substantial effect at high fixed rates, but there was a greater effect at low rates. In particular, for the records where no substantial affect on performance was observed, the records in question were relatively uniform in their noise level. Conversely, for the records where performance effects were observed at low rates, the records had numerous instances of short noisy bursts. As will be appreciated, additional delay increases the buffer size. At low rates the bigger buffer helps the system to deal with the noisy bursts. The buffer is usually nearly empty, but fills up when needed during the burst, and is then emptied again when the burst is over.

In certain of the test regimes, records were compressed for a fixed rate of 5 and 6 bits per sample respectively. At 5 bits per sample, there was some distortion over the entire duration measured, and the distortion grew slightly when the original signals became more noisy. At 6 bits per sample, there was still some distortion when the original signal is noisy for the most problematic signals. However, almost no distortion was observed elsewhere. Almost all tested records in the MIT-BIH Arrhythmia database were reconstructed perfectly when using a fixed-rate of 6 bits per sample.

Certain of the goals for the BTP system 48 are to provide lossless compression a high percentage of the time and to provide good signal quality a high percentage of the time.

To assess performance of the BTP system 48 with regard to these goals. the Percent Root Difference (PRD) for reconstructed ECG signals was measured over each 1 second interval. PRD is essentially RMS error given as a percentage of the RMS of the original signal. In this assessment, the normalizing denominator is still the sum-square of the entire original signal. Cumulative histograms for tested signals were constructed for fixed rates of 5 and 6. Based on this testing, it was observed that with a fixed rate of 5.0 about 90% of the 1 sec. intervals are perfect (a PRD of 0). In addition, it was observed that less than 1% of the 1 sec. intervals have a PRD greater than 1. It was observed that, even for records that were hard to compress, the 1 sec. intervals that showed evidence of distortion still showed relatively little distortion.

While the preceding describes examples of a compression approach as it might pertain to ECG data, it will be appreciated that the present compression approach is also applicable to other types of data where generally lossless compression, fixed data transmission rate, and real-time monitoring are desired, such as other types of medical or monitoring data, or electroencephalography (EEG) data.

Technical benefits of the invention include generally lossless compression of data suitable for use in a real-time, remote monitoring application. In one embodiment, the real-time monitoring application is subject to a fixed-delay transmission constraint. In one implementation, a specific set partitioning method (e.g., binary tree partitioning) is employed on blocks of data that are wavelet transformed in a reversible manner so that encoded blocks may be transmitted losslessly or truncated and transmitted with some loss.

This written description uses examples to disclose the subject matter of interest, including the best mode, and also to enable any person skilled in the art to practice the present approaches, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for compressing an electrocardiograph (ECG) data input acquired by an ECG system, comprising:
    receiving one or more ECG inputs via a data acqusition component of the ECG system;
    on a data processing component of the ECG system, processing the ECG inputs to generate a series of blocks;
    on the data processing component of the ECG system, applying a forward wavelet transform to the blocks to generate a set of wavelet coefficients;
    on the data processing component of the ECG system, applying a compression algorithm to the wavelet coefficients to generate a plurality of blocks of compressed data;
    on the data processing component of the ECG system, truncating compressed blocks of data that are too large to be written to an output buffer of the ECG system; and
    writing the plurality of blocks of compressed data to the output buffer of the ECG system for subsequent transmission by a transmission component of the ECG system.

2. The method of claim 1, wherein the series of blocks are staggered over time.

3. The method of claim 1, wherein the compression algorithm comprises a binary tree partitioning algorithm.

4. The method of claim 3, wherein the binary tree partitioning algorithm is implemented using an integer lifting-based algorithm.

5. The method of claim 1, wherein applying the compression algorithm to the wavelet coefficients to generate the set of compressed data comprises applying a binary tree partitioning algorithm to a plurality of blocks of wavelet coefficients to generate a plurality of respective variable length bitstreams.

6. One or more non-transitory computer-readable media provided as a storage component of an electrocadiograph (ECG) system, the storeage component encoding one or processor-executable routines, wherein the one or more routines, when executed by a data processing component of the ECG system, cause acts to be performed comprising:
    receiving one or more ECG inputs via a data acqusition component of the ECG system;
    on the data processing component of the ECG system, processing the ECG inputs to generate a series of blocks;
    on the data processing component of the ECG system, applying a forward wavelet transform to the blocks to generate a set of wavelet coefficients;

on the data processing component of the ECG system, applying a compression algorithm to the wavelet coefficients to generate a plurality of blocks of compressed data;

on the data processing component of the ECG system, truncating compressed blocks of data that are too large to be written to an output buffer of the ECG system; and writing the plurality of blocks of compressed data to the output buffer of the ECG system for subsequent transmission by a transmission component of the ECG system.

7. The one or more non-transitory computer-readable media of claim 6, wherein the compression algorithm comprises a binary tree partitioning algorithm.

8. The one or more non-transitory computer-readable media of claim 7, wherein the binary tree partitioning algorithm is implemented using an integer lifting-based algorithm.

9. The one or more non-transitory computer-readable media of claim 6, wherein applying the compression algorithm to the wavelet coefficients to generate the set of compressed data comprises applying a binary tree partitioning algorithm to a plurality of blocks of wavelet coefficients to generate a plurality of respective variable length bitstreams.

10. A method for compressing electrocardiograph (ECG) data, comprising:

receiving one or more ECG inputs via a data acqusition component of the ECG system;

on a data processing component of the ECG system, processing the inputs to generate a series of blocks;

on the data processing component of the ECG system, applying a forward wavelet transform to the blocks to generate a set of wavelet coefficients;

on the data processing component of the ECG system, applying a binary tree partitioning compression algorithm to the wavelet coefficients to generate a plurality of blocks of compressed data; and writing the compressed data to a buffer of the ECG system without truncation for subsequent transmission by a transmission component of the ECG system.

11. The method of claim 10, wherein the forward wavelet transform is implemented using a lifting algorithm.

12. The method of claim 10, wherein the series of blocks are staggered over time.

13. One or more non-transitory computer-readable media provided as a storage component of an electrocadiograph (ECG) system, the storeage component encoding one or processor-executable routines, wherein the one or more routines, when executed by a data processing component of the ECG system, cause acts to be performed comprising:

receiving one or more ECG inputs via a data acqusition component of the ECG system;

on the data processing component of the ECG system, processing the inputs to generate a series of blocks;

on the data processing component of the ECG system, applying a forward wavelet transform to the blocks to generate a set of wavelet coefficients;

on the data processing component of the ECG system, applying a binary tree partitioning compression algorithm to the wavelet coefficients to generate a plurality of blocks of compressed data; and writing the compressed data to a buffer of the ECG system without truncation for subsequent transmission by a transmission component of the ECG system.

14. The one or more non-transitory computer-readable media of claim 13, wherein the forward wavelet transform is implemented using a lifting algorithm.

* * * * *